United States Patent [19]

McCaully et al.

[11] 4,065,451
[45] Dec. 27, 1977

[54] 1,3-DIHYDRO-3-HYDROXY-5-PHENYL-2H-1,4-BENZODIAZEPIN-2-ONE, SUBSTITUTED DIAMINO ACETATE ESTERS AND THEIR ACID SALTS

[75] Inventors: Ronald J. McCaully, Malvern; Abraham Nudelman, Bala Cynwyd; Stanley C. Bell, Penn Valley, all of Pa.

[73] Assignee: American Home Products, New York, N.Y.

[21] Appl. No.: 223,712

[22] Filed: Feb. 4, 1972

Related U.S. Application Data

[63] Continuation-in-part of Ser. No. 129,638, March 30, 1971, abandoned.

[51] Int. Cl.² ............... C07D 243/24; C07D 403/12
[52] U.S. Cl. ............... 260/239.3 D; 424/244;
424/250; 424/256; 424/267; 424/274;
424/248.54; 424/251; 424/273 R; 424/273 P;
260/243.3
[58] Field of Search ............... 260/239.3 D

[56] References Cited

U.S. PATENT DOCUMENTS

| | | | |
|---|---|---|---|
| 3,296,249 | 1/1967 | Bell | 260/239.3 D |
| 3,391,138 | 7/1968 | Archer et al. | 260/239.3 D |

OTHER PUBLICATIONS

Bell et al., "J. Med. Chem.", vol. 11, pp. 457–461, (1968).

*Primary Examiner*—Natalie Trousof
*Assistant Examiner*—Robert T. Bond
*Attorney, Agent, or Firm*—Richard K. Jackson

[57] ABSTRACT

This invention is directed to novel central nervous system depressants of Formula I

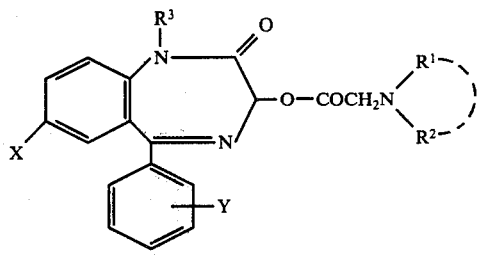

wherein $R^1$ is selected from the group consisting of (lower)alkyl and ar(lower)alkyl; $R^2$ is selected from the group consisting of di(lower)alkylamino(lower)alkyl and diaryl(lower)alkylamino(lower)alkyl; $R^1$ and $R^2$ may be concatenated to form a radical selected from the group consisting of

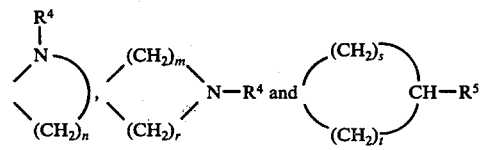

wherein $R^4$ is selected from the group consisting of (lower)alkyl, aryl, hydroxy(lower)alkyl, ar(lower)alkyl and (lower)alkoxy(lower)alkyl; $R^5$ is selected from the group consisting of (lower)-alkylamino and piperidino; $n$ is an integer from 3 to 5; $m$ is an integer from 1–2; $r$ is an integer from 2 to 3; $s$ is an integer from 0 to 6; $t$ is an integer from 0–6; with the proviso that the sum of $s$ and $t$ is 3 to 6; $R^3$ is selected from the group consisting of hydrogen, (lower)alkyl, ar(lower)alkyl and (lower)alkoxy(lower)alkyl; X is selected from the group consisting of halogen, cyano, trifluoromethyl, nitro and (lower)alkylthio; Y is selected from the group consisting of hydrogen, halogen, trifluoromethyl, nitro and (lower)alkylthio; and the pharmaceutically acceptable salts thereof, in addition to the method of their preparation and administration and administrable compositions containing the active compounds.

12 Claims, No Drawings

1,3-DIHYDRO-3-HYDROXY-5-PHENYL-2H-1,4-BENZODIAZEPIN-2-ONE, SUBSTITUTED DIAMINO ACETATE ESTERS AND THEIR ACID SALTS

RELATED APPLICATIONS

This application is a continuation-in-part of Ser. No. 129,638 filed Mar. 30, 1971, now abandoned, by Ronald J. McCaully, Abraham Nudelman and Stanley C. Bell.

DESCRIPTION OF THE INVENTION

This invention relates to the pharmacologically active 1,3-dihydro-3-hydroxy-5-phenyl-2H-1,4-benzodiazepin-2-one, substituted diamino acetates. The chemical structure of these compounds may be schematically represented by Formula I:

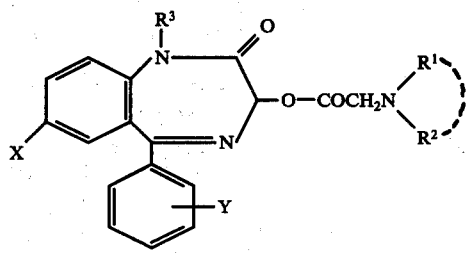

wherein $R^1$ is selected from the group consisting of (lower)alkyl and ar(lower)alkyl; $R^2$ is selected from the group consisting of di(lower)alkylamino(lower)alkyl and diar(lower alkylamino(lower)alkyl; $R^1$ and $R^2$ may form a radical selected from the group consisting of

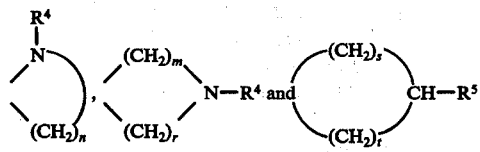

wherein $R^4$ is selected from the group consisting of (lower)alkyl, aryl, hydroxy(lower)alkyl, ar(lower)alkyl and (lower)alkoxy(lower)alkyl; $R^5$ is selected from the group consisting of (lower)alkylamino and piperidino; $n$ is an integer from 3-5; $m$ is an integer from 1-2; $r$ is an integer from 2 to 3; $s$ is an integer from 0-6; $t$ is an integer from 0-6; with the proviso that the sum of $s$ and $t$ must be 3,4,5 or 6; $R^3$ is selected from the group consisting of hydrogen, (lower)alkyl, ar(lower)alkyl and (lower)alkoxy(lower)alkyl; X is selected from the group consisting of halogen, cyano, trifluoromethyl, nitro and (lower)alkylthio; Y is selected from the group consisting of hydrogen, halogen, trifluoromethyl, nitro and (lower)alkylthio; and the pharmaceutically acceptable salts thereof. The hydrated forms of formula I are also within the scope of the invention, the anhydrous and various hydrated forms of each compound being readily prepared by drying the initially formed product.

The term (lower)alkyl is used to include straight and branched chain hydrocarbon groups which contain from one to about six carbon atoms such as methyl, ethyl, i-propyl, n-propyl, n-butyl, n-hexyl and the like. The term (lower)alkoxy is used to include hydrocarbonoxy groups which contain from one to about six carbon atoms such as methoxy, ethoxy, n-propoxy, n-butoxy, n-penoxy and the like. The terms halo and halogen are used to include atoms selected from the group consisting of chlorine, fluorine, bromine and iodine. The terms aryl and arare used to include monovalent, aromatic, hydrocarbon radicals containing 6 to 10 carbon atoms such as phenyl, tolyl and naphthyl. The term pharmaceutically acceptable acid addition salts is used to include those non-toxic acid addition salts which may be formed with both organic and inorganic acids such as hydrochloric, hydrobromic, sulfuric, phosphoric, methane sulfonic, nitric, p-toluene sulfonic, acetic, citric, maleic, succinic and the like.

The compounds of the invention may be prepared by the following reaction scheme:

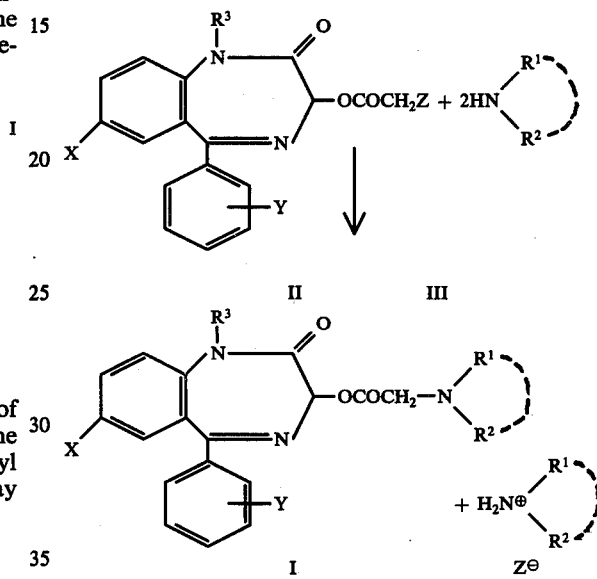

wherein $R^1$, $R^2$, $R^3$, X and Y are the same as hereinabove described and Z is selected from the group consisting of chlorine, bromine and iodine.

The compounds of the invention are prepared by combining a molar quantity of the appropriate 1,3-dihydro-3-hydroxy-5-phenyl-2$\underline{H}$-1,4-benzodiazepin-2-one halo acetate with two to three moles of the appropriately substituted diamine in a nonreactive organic solvent that is capable of dissolving the reactants. Suitable examples include xylene, benzene, toluene and tetrahydrofuran. The reaction is preferably carried out at 25° to 80° C. for about 0.5 to about 24 hours. The reaction solvent is evaporated and the residue is dissolved in a water immiscible organic solvent and is extracted with water.

The organic phase is separated, dried, concentrated and added to a vigorously stirred solution of the appropriate strong pharmaceutically acceptable acid in ether. The compounds of the invention may be filtered and recrystallized from the appropriate solvent.

The compounds of the invention are physiologically active central nervous system depressants.

In the pharmacological evaluation of the biological activity of compounds of this invention, the in vivo effects were tested as follows: The compounds tested were administered orally or intraperitoneally to three mice (14 to 24 grams) at doses ranging from 0.04 to 400 milligrams per kilogram of host body weight (MPK). The animals were watched for a minimum of two hours during which time signs of general stimulation (i.e., increased spontaneous motor activity, hyperactivity on tactile stimulation, twitching), general depression (i.e., decreased spontaneous motor activity, decreased respiration) and autonomic activity (i.e., miosis, mydriasis, diarrhea) were noted.

Compounds of this invention induce central nervous system depressant effects at dosages of 4.0 MPK per os and lower in the above mentioned host. Thus the compounds of the invention, have demonstrated utility as physiologically active compounds in experimental and comparative pharmacology and are of value in the treatment of mammals, e.g., mice, rats, etc., who are responsive to treatment with central nervous system depressant agents. Specifically the compounds may be administered for the purpose of inducing a calming effect in mammals.

It is particularly important to note that the compounds of the invention are water soluble. This property is of especial significance in preparing dosage formulations wherein a liquid vehicle is required, either for oral or parenteral administration, where the use of a solid drug is not feasible or is contra-indicated as in pre-operative medication where material in the alimentary tract is to be avoided or in the case of a patient unable to swallow a pill or ingest from a solid formulation as in the case of one suffering from delerium tremens.

When the compounds of the invention are employed as described above they may be administered alone or in combination with pharmacologically acceptable carriers, the proportion of which is determined by the chosen route of administration and standard pharmaceutical practice. For example, they may be administered orally in tablet or capsule form with conventional flavors, diluents, lubricants, disintegrators or binding agents as may be required. They may be administered orally in the form of a solution or they may be injected parenterally. For parenteral administration they may be used in the form of a sterile solution containing other solutes, for example, enough saline or glucose to make the solution isotonic. It is most advantageous to provide the compound as a dry powder in a suitable container so that it may be admixed with a suitable aqueous vehicle prior to administration.

A suitable tablet formulation is as follows:

| | |
|---|---|
| 7-chloro-5-(o-chlorophenyl)-1,3-dihydro-3-hydroxy-2H-1,4-benzodiazepin-2-one, 4-methyl-1-piperazineacetate, dihydro-chloride dihydrate | 5 mg |
| Microcrystalline Cellulose, N.F. | 20 mg |
| Magnesium Stearate, U.S.P. | 0.25 mg |
| Lactose, U.S.P. | 74.75 mg |
| Total Tablet Weight | 100 mg |

A suitable reconstitutable injectable formulation is as follows:

1. 7-chloro-5-(o-chlorophenyl)-1,3-dihydro-3-hydroxy-2H-1,4-benzodiazepin-2-one, 4-methyl-1-piperazineacetate, dihydrochloride dihydrate . . . 5 mg (packaged with 95 mg. of lactose in a sealed glass ampoule)
2. Vehicle: Sterile water for Injection 5 ml containing benzyl alcohol 1% and sodium acetate/acetic acid buffer 0.6%

In general, the unit dosage form will contain from 0.5 to 35 milligrams of the active ingredient, the remainder of the formulation constituting known adjuvants. In human treatment, from 1 to 10 milligram and conventionally 5 milligram doses of the active compounds of this invention are considered to be most desirable from the standpoint of uniform presentation for controlled administration.

The following examples are added to illustrate but not to necessarily limit the scope of the invention.

EXAMPLE I

7-Chloro-5-(o-chlorophenyl)-1,3-dihydro-3-hydroxy-2H-1,4-benzodiazepin-2-one, chloroacetate A mixture of 7-chloro-5-(o-chlorophenyl)-1,3-dihydro-2H-1,4-benzodiazepin-2-one, 4-oxide (16 g, 0.05 mole) and chloroacetic anhydride (25 g, 0.145 mole) was heated with stirring at 100°–110° for 2.5 hours. Ether was then added and the mixture was stirred for 10 minutes. The solid obtained (14.7 g, 75% yield) was filtered, washed with ether and recrystallized from dichloromethane-ether, mp. 232°–234°, nmr (DMSO-$D_6$) ppm ($\delta$); 4.72 (s, 2); 6.10 (s, 1); 7.17 (d, 1); 7.4-8 (m, 6).

Anal. Calcd for $C_{17}H_{11}Cl_3N_2O_3$: C, 51.35; H, 2.79; N, 7.05. Found: C, 51.26; H, 2.83; N, 6.94.

Following the procedure of the preceding paragraph react 7-chloro-1,3-dihydro-5-phenyl-2H-1,4-benzodiazepin-2-one, 4-oxide with chloroacetic anhydride to produce 7-chloro-1,3-dihydro-3-hydroxy-5-phenyl-2H-1,4-benzodiazepin-2-one, chloroacetate.

EXAMPLE 2

7-Chloro-5-(o-chlorophenyl)-1,3-dihydro-3-hydroxy-1-methyl-2H-1,4-benzodiazepin-2-one, chloroacetate This compound was prepared by the same procedure as the one described for Example I from 7-chloro-5-(o-chlorophenyl)-1,3-dihydro-1-methyl-2H-1,4-benzodiazepin-2-one, 4-oxide (6.7 g, 0.02 mole) and chloroacetic anhydride (12 g, 0.07 mole). The obtained product (6.8 g, 82.6% yield) had mp. 172°–174°, nmr (DCCl$_3$), ppm. ($\delta$); 3.51 (s, 3); 4.41 (s, 2); 6.15 (s, 1); 7.19 (d, 1); 7.4–8 (m, 6).

Anal. Calcd for $C_{18}H_{13}N_2Cl_3O_3$: C, 52.52; H, 3.18; N, 6.80; Cl, 25.84. Found: C, 52.27; H, 3.37; N, 6.61; Cl, 25.72.

EXAMPLE 3

7-Chloro-5-(o-chlorophenyl)-1,3-dihydro-3-hydroxy-1-methyl-2H-1,4-benzodiazepin-2-one, chloroacetate To a solution of 7-chloro-5-(o-chlorophenyl)-1,3-dihydro-3-hydroxy-1-methyl-2H-1,4-benzodiazepine-2-one (10 g, 0.03 mole) and 4-dimethylamino-pyridine (3.66 g, 0.03 mole) in 200 ml of tetrahydrofuran, was added chloroacetyl chloride (3.39 g, 0.03 mole). A very heavy precipitate formed instantly. After 10 minutes of stirring, no trace of 7-chloro-5-o-chlorophenyl)-1,3-dihydro-3-hydroxy-1-methyl-2H-1,4-benzodiazepine-2-one could be detected by thin layer chromatography (silica plates using ether as eluent). The precipitate was filtered off and the filtrate was flash evaporated, to give an oil which crystallized upon addition of ether. Collected 12.1 g (99% yield). The mp, ir and nmr spectra of this product were identical to those described above in Example 2.

Following the procedure of the preceding paragraph, 7-chloro-1,3-dihydro-3-hydroxy-1-methyl-5-phenyl-2H-1,4-benzodiazepin-2-one reacts with chloroacetyl chloride to produce the corresponding chloroacetate.

EXAMPLE 4

7-Chloro-5-(o-chlorophenyl)-1,3-dihydro-3-hydroxy-2H-1,4-benzodiazepin-2-one, 4-methyl-1-piperazineacetate, dihydrochloride dihydrate A solution of the compound prepared in Example 1 (3 g, 7.5 moles) and N-methylpiperazine (3 ml) in 50 ml of anhydrous tetrahydrofuran was stirred for 16 hours at room temperature. The solvent was flash evaporated and the residue dissolved in dichloromethane was washed repeatedly with saturated aqueous sodium chloride. The organic phase was dried and concentrated to a total volume of 5 ml which was then added to a vigorously stirred solution of gaseous hydrogen chloride in ether. The obtained solid was recrystallized from methanol-ether, collected 1.5 g (35% yield), mp. 202°–204° d, nmr (DMSO-$D_6$), ppm (δ), 2.80 (s, 3); 3.40 (broad s, 8); 4.23 (s, 2); 5.98 (s, 1); 6.96 (d, 1); 7.2–7.8 (m, 6).

Anal. Calcd for $C_{22}H_{22}Cl_2N_4O_3.2HCl.2H_2O$: C, 46.33; H, 4.95; N, 9.82; $H_2O$, 6.32. Found: C, 46.11; H, 4.34; N, 9.85; $H_2O$, 6.40.

The dihydrochloride was soluble in water up to about 30 milligrams per milliliter at room temperature (25° C).

EXAMPLE 5

7-Chloro-5-(o-chlorophenyl)-1,3-dihydro-3-hydroxy-1-methyl-2H-1,4-benzodiazepin-2-one, 4-methyl-1-piperazineacetate, dihydrochloride, sesquihydrate This compound was prepared as described in Example 4 from the compound prepared in Example 2 (5 g, 0.012 mole) and N-methylpiperazine. The product obtained (2.5 g, 36% yield) decomposed above 210°, nmr (DMSO-$D_6$) ppm (δ), 2.82 (s, 3); 3.43 (broad s, 11); 4.27 (s, 2); 6.00 (s, 1); 7.07 (d, 1); 7.4–8 (m, 6).

Anal. Calcd for $C_{23}H_{24}Cl_2N_4O_3.2HCl.1\ 1/2H_2O$: C, 48.02: H, 5.08; N, 9.74. Found: C, 47.88; H, 4.89; N, 9.78.

The dihydrochloride salt was soluble in water in an amount up to about 30 milligrams per milliliter at room temperature (25° C.)

EXAMPLE 6

7-Chloro-5-(o-chlorophenyl)-1,3-dihydro-3-hydroxy-2H-1,4-benzodiazepin-2-one, N-(2-dimethylaminoethyl)-N-methylglycinate, dihydrochloride, dihydrate The title compound was prepared by the same procedure as that described in Example 4 from the compound prepared in Example 1 and N,N,N'-trimethylethylenediamine. The product was obtained in 20% yield from ethanol-ether, mp 221°–223° d, nmr (DMSO-$D_6$), ppm(δ), 2.95 (s,6), 3.00 (s, 3), 3.65 (broad s, 4), 4.52 (broad s, 2), 6.10 (s, 1), 7.02 (d, 1), 7.4–7.8 (m, 6).

Anal. Calcd for $C_{22}H_{24}Cl_2N_4O_3.2HCl.2H_2O$: C, 46.17; H, 5.28; N, 9.79. Found: C, 45.96; H, 5.36; N, 9.85.

EXAMPLE 7

7-Chloro-5-(o-chlorophenyl)-1,3-dihydro-3-hydroxy-2H-1,4-benzodiazepin-2-one, 4-(hydroxyethyl)-1-piperazineacetate, dihydrochloride, 2½ hydrate The title compound was prepared by the same procedure as that described in Example 4 from the compound prepared in Example 1 and N-(2-hydroxyethyl)-piperazine. The product was obtained in 46% yield from ethanol-ether, it became dark above 195° and decomposed above 202°, nmr (DMSO-$D_6$), ppm(δ), 3.1–4.2 (broad m, 16), 4.55 (broad s, 2), 6.03 (s, 1), 7.01 (d, 1), 7.3–7.8 (m, 6).

Anal. Calcd for $C_{23}H_{26}Cl_4N_4O_4.2HCl.2½H_2O$: C, 45.33; H, 5.13; N, 9.29; $H_2O$, 7.39. Found: C, 45.34; H, 4.70; N, 9.33; $H_2O$, 7.39.

EXAMPLE 8

By a procedure analogous to that described in Example 4 the following compounds in which $R^1$ and $R^2$ are concatenated may be prepared.

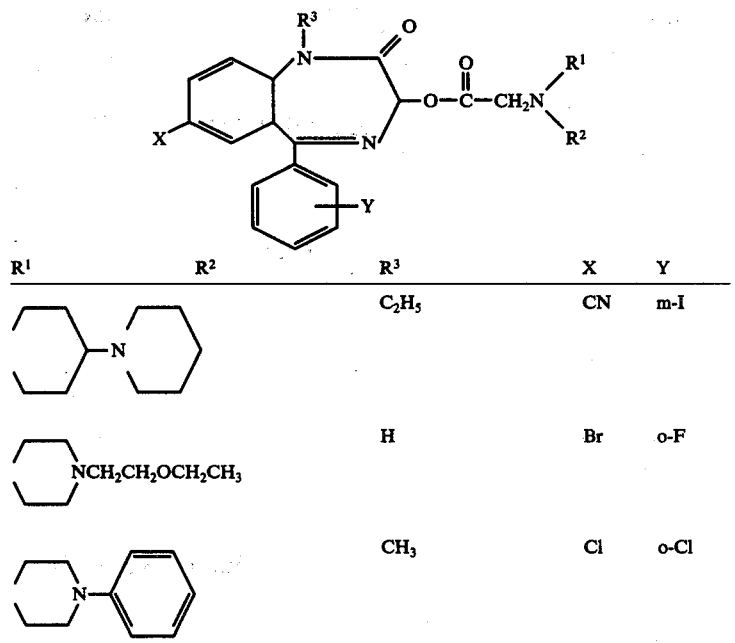

-continued

[Structure: benzodiazepine core with R³ on N, phenyl with Y substituent, X on benzene ring, and ester linkage —O—C(=O)—CH₂N(R¹)(R²)]

| R¹ | R² | R³ | X | Y |
|---|---|---|---|---|
| | | CH₂C₆H₅ | CN | p-Cl |
| piperidine-N—CH₂— | phenyl | | | |
| | CH₃ | CH₃ | Cl | H |
| azepane-N— | | | | |
| | C₂H₅ | H | Br | o-Cl |
| azepane-N— | | | | |
| | CH₂—CH₂—CH₃ | CH₂C₆H₅ | CN | o-F |
| pyrrolidine-N— | | | | |
| | | CH₂CH₂—OCH₃ | Cl | p-Cl |
| azepane-N—CH₂CH₂—OH | | | | |
| | | CH₂CH₂—CH₃ | Br | o-Cl |
| piperidine-N—CH₂CH₂— | phenyl | | | |
| | H | | CN | m-I |
| piperidine-N—CH₃ | | | | |
| | | CH₂OCH₂CH₃ | Cl | o-Cl |
| piperidine-N—(CH₂—CH₃)₂ | | | | |
| | | CH₂—CH₃ | Br | o-F |
| piperidine-N—CH₂—CH₂—CH₃ | | | | |
| | (CH₃)₂ | H | Cl | p-Cl |
| pyrrolidine-N— | | | | |
| | | CH₂—CH₂—O—CH₃ | CN | o-Cl |
| pyrrolidine-N—(CH₃)₂ | | | | |

-continued

[Structure: benzodiazepine with R³ on N, X substituent, phenyl with Y, and -O-C(=O)-CH₂-N(R¹)(R²) group]

| R¹ | R² | R³ | X | Y |
|---|---|---|---|---|
| [cyclooctyl]-N-(CH₃)₂ | | CH₃ | Br | o-Br |
| | [cyclooctyl]-N-(CH₂-CH₃)₂ | CH₂CH₃ | CN | o-Cl |
| N-(CH₃)₂ [cyclooctyl] | | CH₂C₆H₅ | Cl | p-Br |

EXAMPLE 9

By a procedure analogous to that described in Example 4 the following compounds may be prepared.

[Structure: benzodiazepine with R³ on N, X substituent, phenyl with Y, and -OCOCH₂N(R¹)(R²) group]

| R¹ | R² | R³ | X | Y |
|---|---|---|---|---|
| —CH₂CH₃ | CH₂CH₂N(CH₂—CH₃)(CH₂CH₃) | —CH₃ | Cl | o-Cl |
| —CH₃ | CH₂CH₂CH₂N(CH₃)(CH₃) | H | NO₂ | H |
| —CH₃ | —CH₂CH₂N(morpholino) | H | Cl | O-Cl |
| —CH₂CH₃ | —CH₂CH₂N(N-methylpiperazino) | —CH₂CH₂O-n-CH₂CH₂CH₂CH₃ | —SCH₃ | o-Br |
| —CH₂CH₃ | —CH₂CH₂—N(pyrrolidino) | —CH₂C₆H₅ | Br | p-Br |

-continued
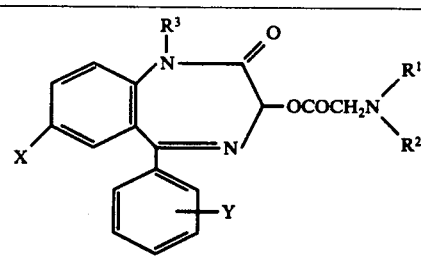
| R¹ | R² | R³ | X | Y |
|---|---|---|---|---|
| —CH₂CH₃ | 3-methylquinuclidinyl | —CH₂CH₃ | CN | m-I |
| —CH₃ | CH₂CH₂CH₂—N(carbazolyl) | —CH₃ | Cl | o-Cl |
| —CH₂—C₆H₅ | —CH₂—N(CH₃)₂ | —CH₃ | Cl | o-Cl |
| —CH₂—CH₃ | —CH₂—CH₂—N(CH₃)₂ | —CH₂—C₆H₅ | NO₂ | H |
| —CH₂—CH₂—CH₃ | —CH₂—CH₂—N(CH₂—CH₃)₂ | H | Br | o-Br |
| —CH₂—CH₂—C₆H₅ | —CH₂—CH₂—N(CH₂—C₆H₅)₂ | CH₃OCH₂— | Cl | p-Br |
| —CH₂—C₆H₅ | —CH₂—CH₂—N(CH₂—CH₂—C₆H₅)₂ | CH₃—CH₂— | CN | o-Cl |
| —CH₂—CH₃ | —CH₂—N(CH₂—C₆H₅)₂ | CH₃CH₂— | NO₂ | o-Cl |

-continued

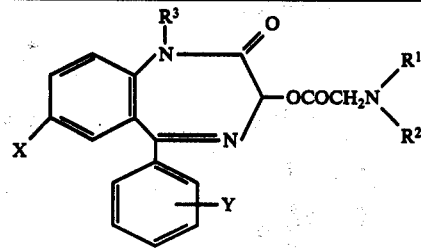

| R¹ | R² | R³ | X | Y |
|---|---|---|---|---|
| —CH₃ | —CH₂—CH₂N(CH₂CH₂CH₃)(CH₂CH₂CH₃) | CH₃—CH₂—CH₂ | Br | p-I |
| —CH₂CH₃ | —CH₂—CH₂—N(CH₃)(CH₃) | —H | Cl | p-Cl |

EXAMPLE 10

7-Chloro-5-(o-chlorophenyl)-1,3-dihydro-3-hydroxy-2H-1,4-benzodiazepin-2-one, 4-methyl-1-piperazineacetate, hydrochloride, hydrate An aqueous solution of 7-chloro-5-(o-chlorophenyl)-1,3-dihydro-3-hydroxy-2H-1,4-benzodiazepin-2-one, 4-methyl-1-piperazineacetate, dihydrochloride,dihydrate (29 g., 0.05 mole) prepared as described in Example 4, was neutralized with an excess of 1N sodium hydroxide and was extracted with dichloromethane. The organic phase was dried and evaporated to give a fine white powder, 18.5 g. (80% yield), nmr (DCCl₃), ppm (δ), 2.27 (s, 3), 2.55 (broad s,4), 2.70 (broad s, 4), 3.57 (s, 2), 6.08 (s, 1), 7.08 (d, 1), 7.2–7.9 (m, 6).

A solution of equimolar quantities of 7-chloro-5-(o-chlorophenyl)-1,3-dihydro-3-hydroxy-2H-1,4-benzodiazepin-2-one, 4-methyl-piperazineacetate, dihydrochloride, dihydrate and the above obtained free base (2.3 millimoles of each) in methanol was stirred at room temperature for 30 min. The solvent was flash evaporated and the residual foam was recrystallized from methanol ether, to give 2 g. (82% yield) of white solid, mp. 233°–234° C, nmr (DMSO-D₆), ppm (δ), 2.81 (s, 3), 3.05 (broad m, 4), 3.35 (broad m, 4), 3.67 (s,2), 5.95 (s, 1), 7.00 (d, 1), 7.3-7.8 (m, 6).

Anal. Calcd. for C₂₂H₂₂Cl₂N₄O₃.HCl.H₂O: C, 51.22; H, 4.89; N, 10.86; Cl, 20.62. Found: C, 51.44; H, 4.56; N, 10.74; Cl, 20.91.

By repeating the foregoing technique for producing a monohydrochloride salt, employing 7-chloro-1,3-dihydro-3-hydroxy-5-phenyl-2H-1,4-benzodiazepin-2-one, chloroacetate or 7-chloro-1,3-dihydro-3-hydroxy-1-methyl-5-phenyl-2H-1,4-benzodiazepin-2-one, chloroacetate as the initial reactant, the corresponding 5-phenyl and 1-methyl-5-phenyl analogues of the title compound are prepared.

EXAMPLE 11

7-Chloro-5-(o-chlorophenyl)-1,3-dihydro-3-hydroxy-2H-1,4-benzodiazepin-2-one, 4-methyl-1-piperazineacetate, methane sulfonate, hydrate To a solution of 7-chloro-5-(o-chlorophenyl)-1,3-dihydro-3-hydroxy-2H-1,4-benzodiazepin-2-one, 4-methyl-1-piperazineacetate (2.3 g., 5 millimoles) prepared as described in Example 10, was added methane sulfonic acid (0.48 g., 5 millimoles). The solution was stirred at room temperature for 30 min. The solvent was then flash evaporated and the residue was recrystallized from methanol-ether to give 2.3 g. (80% yield) of white crystalline product which did not melt sharply but slowly decomposed above 160°, nmr (DMSO-D₆), ppm (δ), 2.42 (s, 3), 2.82 (s, 2), 3.0 (broad m, 4), 3.4 (broad m, 4), 3.65 (s, 2), 5.95 (s,1), 7.05 (d, 1), 7.2-7.9 (m, 6).

Anal. Calcd. for C₂₂H₂₂Cl₂N₄O₃.CH₄SO₃.H₂O: C, 48.00; H, 4.90; N, 9.74; Cl, 12.32. Found: C, 48.08; H, 4.71; N, 9.41; Cl, 12.62.

The methane sulfonate salt was soluble in water in amounts greater than 300 milligrams per milliliter at room temperature (25° C.)

By repeating the foregoing technique for producing a methane sulfonate salt employing 7-chloro-1,3-dihydro-3-hydroxy-5-phenyl-2H-1,4-benzodiazepin-2-one, chloroacetate or 7-chloro-1,3-dihydro-3-hydroxy-1-methyl-5-phenyl-2H-1,4-benzodiazepin-2-one, chloroacetate as the initial reactant, the corresponding 5-phenyl and 1-methyl-5-phenyl analogues of the title compound are prepared.

EXAMPLE 12

7-Chloro-5-(o-chlorophenyl)-1,3-dihydro-3-hydroxy-2H-1,4-benzodiazepin-2-one, 4-methyl-1-piperazineacetate, maleate, hemihydrate To a methanolic solution of 7-chloro-5-(o-chlorophenyl)-1,3-dihydro-3-hydroxy-2H-1,4-benzodiazepin-2-one, 4-methyl-1-piperazineacetate (2.3 g., 5 mmoles) prepared as described in Example 10, was added maleic acid (0.58 g., 5 mmole). The solution was stirred at room temperature for 30 min. The solvent was then flash evaporated and the residue was recrystallized from methanol-ether to give 1.5 g. (51% yield) of white crystalline product which did not melt sharply but slowly decomposed above 125°, nmr (DMSO-D₆), ppm (δ), 2.92 (s, 3), 3.0 (broad s, 4), 3.4 (broad s, 4), 3.63 (s, 2), 6.02 (s, 1), 6.30 (s, 2), 7.1 (d, 1), 7.4–7.9 (m, 6).

Anal. Calcd. for $C_{22}H_{22}Cl_2N_4O_2 \cdot C_4H_4O_4 \cdot \frac{1}{2}H_2O$: C, 53.25; H, 4.64; N, 9.55; Cl, 12.09. Found: C, 52.96; H, 4.53; N, 9.46; Cl, 11.96.

EXAMPLE 13

7-Chloro-5-(o-chlorophenyl)-1,3-dihydro-3-hydroxy-1-methyl-2$\underline{H}$-1, 4-benzodiazepin-2-one, 4-methyl-1-piperazineacetate, hydrochloride, hydrate An aqueous solution of 7-chloro-5-(o-chlorophenyl)-1,3-dihydro-3-hydroxy-1-methyl-2$\underline{H}$-1, 4-benzodiazepin-2-one,4-methyl-1-piperazineacetate, dihydrochloride, sesquihydrate (11.6 g, 0.02 mole) prepared as described in Example 5, was neutralized with an excess of 1N sodium hydroxide and was extracted with dichloromethane. The organic phase was dried and evaporated to give a fine powder 9.1 g. (94.6% yield); nmr (DCCl$_3$) ppm ($\delta$), 2.27 (s, 3), 2.57 (broad m, 4), 2.65 (broad m, 4), 3.46 (s, 3), 3.55 (s, 2), 6.10 (s, 1), 7.10 (d, 1), 7.2–7.9 (m, 6).

A solution of equimolar quantities of 7-chloro-5-(o-chlorophenyl)-1,3-dihydro-3-hydroxy-1-methyl-2$\underline{H}$-1,4-benzodiazepin-2-one, 4-methyl-1-piperazineacetate, dihydrochloride, sesquihydrate, and the above obtained free base (20 millimoles of each) in methanol was stirred at room temperature for 30 min. The solvent was flash evaporated and the residual foam was recrystallized from methanol ether, to give 15 g. (71% yield) of solid, mp. 270°–271° C; nmr (DMSO-D$_6$) ppm ($\delta$) 2.87 (s, 3), 3.1 (broad m, 4), 3.4 (broad m, 4), 3.49 (s, 3), 3.70 (s, 2), 6.07 (s, 1), 7.12 (d, 1), 7.5–7.9 (m, 6).

Anal. calcd. for $C_{23}H_{24}Cl_3N_4O_3 \cdot HCl \cdot H_2O$: C, 51.13; H, 5.14; N, 10.57; Cl, 20.08. Found: C, 52.34; H, 4.75; N, 10.56; Cl, 20.64.

The monohydrochloride salt was soluble in water in an amount up to about 30 milligrams per milliliter at room temperature (25° C).

EXAMPLE 14

7-Chloro-5-(o-chlorophenyl)-1,3-dihydro-3-hydroxy-1-methyl-2$\underline{H}$-1,4-benzodiazepin-2-one, 4-methyl-1-piperazineacetate, methanesulfonate To a solution of 7-chloro-5-(o-chlorophenyl)-1,3-dihydro-3-hydroxy-1-methyl-2$\underline{H}$-1,4-benzodiazepin-2-one, 4-methyl-1-piperazineacetate (197.5 g, 0.4 moles) prepared as described in Example 13, was added methane sulfonic acid (38.8 g., 0.4 moles). The solution was stirred at room temperature for 30 minutes. The solvent was then flash evaporated and the residue was recrystallized from methanol ether to give 196 g. (85.5% yield) of white crystalline product, m.p. 238°–241°, nmr (DMSO-D$_6$) ppm ($\delta$), 2.48 (s, 3), 2.87 (s, 3), 3 (broad m, 4), 3.3 (broad m, 4), 3.48 (s, 3), 3.68 (s, 2), 6.02 (s, 1), 7.10 (m, 1), 7.5–7.95 (m, 6).

Anal. Calcd. for $C_{23}H_{24}Cl_2N_4O_3 \cdot CH_4SO_3$: C, 50.44; H, 4.94; N, 9.80; Cl, 12.41; S, 5.61. Found: C, 50.32; H, 4.94; N, 9.77; Cl, 12.41; S, 5.67.

The methane sulfonate salt was soluble in water at room temperature (25° C) in amounts up to and exceeding 300 milligrams per milliliter.

What we claim is:

1. A compound selected from the group consisting of

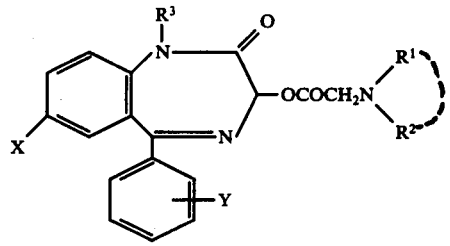

wherein
- R$^1$ is a member selected from the group consisting of alkyl of 1 to 6 carbon atoms and hydrocarbyl aralkyl of 7 to 16 carbon atoms;
- R$^2$ is a member selected from the group consisting of dialkylaminoalkyl of 3 to 18 carbon atoms, and hydrocarbyl diaralkylaminoalkyl of 14 to 32 carbon atoms;
- R$^1$ and R$^2$, when taken together form a member selected from the group consisting of

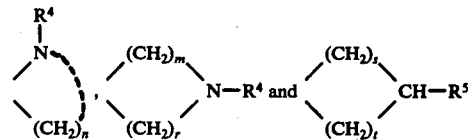

wherein R$^4$ is a member selected from the group consisting of alkyl of 1 to 6 carbon atoms, hydrocarbyl aryl of 6 to 10 carbon atoms, hydroxyalkyl of 1 to 6 carbon atoms, hydrocarbyl aralkyl of 7 to 16 carbon atoms and alkoxyalkyl of 2 to 12 carbon atoms;
- R$^5$ is a member selected from the group consisting of alkylamino of 1 to 6 carbon atoms and piperidino; $n$ is one of the integers 3, 4 or 5; $m$ is one of the integers 1 or 2; $r$ is one of the integers 2 or 3; $s$ is an integer from 0 to 6; $t$ is an integer from 0 to 6; with the proviso that the sum of s and t must be at least 3 and not more than 6;
- R$^3$ is a member selected from the group consisting of hydrogen, alkyl of 1 to 6 carbon atoms, hydrocarbyl aralkyl of 7 to 12 carbon atoms and alkoxy alkyl of 2 to 12 carbon atoms;
- X is a member selected from the group consisting of halogen, cyano, trifluoromethyl, nitro and alkylthio of 1 to 6 carbon atoms;
- Y is a member selected from the group consisting of hydrogen, halogen, trifluoromethyl, nitro and alkylthio of 1 to 6 carbon atoms; and the pharmaceutically acceptable salts thereof.

2. A compound as defined in claim 1 which is a hydrochloride salt of 7-chloro-5-(o-chlorophenyl)-1,3-dihydro-3-hydroxy-2$\underline{H}$-1,4-benzodiazepin-2-one, 4-methyl-1-piperazineacetate.

3. A compound as defined in claim 1 which is a hydrochloride salt of 7-chloro-5-(o-chlorophenyl)-1,3-dihydro-3-hydroxy-1-methyl-2$\underline{H}$-1,4-benzodiazepin-2-one, 4-methyl-1-piperazineacetate.

4. A compound as defined in claim 1 which is a hydrochloride salt of 7-chloro-5-(o-chlorophenyl)-1,3-dihydro-3-hydroxy-2$\underline{H}$-1,4-benzodiazepin-2-one, N-(2-dimethylaminoethyl)-N-methylglycinate.

5. A compound as defined in claim 1 which is a hydrochloride salt of 7-chloro-5-(o-chlorophenyl)-1,3- dihydro-3-hydroxy-2H-1,4-benzodiazepin-2-one, 4-(hydroxyethyl)-1-piperazineacetate.

6. A compound as defined in claim 1 which is a methanesulfonate salt of 7-chloro-5-(o-chlorophenyl)-1,3-dihydro-3-hydroxy-2H-1,4-benzodiazepin-2-one, 4-methyl-1-piperazineacetate.

7. A compound as defined in claim 1 which is a methanesulfonate salt of 7-chloro-5-(o-chlorophenyl)-1,3-dihydro-3-hydroxy-1-methyl-2H-1,4-benzodiazepin-2-one, 4-methyl-1-piperazineacetate.

8. A compound as defined in claim 1 which is a maleic acid salt of 7-chloro-5-(o-chlorophenyl)-1,3-dihydro-3-hydroxy-2H-1,4-benzodiazepin-2-one, 4-methyl-1-piperazineacetate.

9. A compound as defined in claim 1 which is a hydrochloride salt of 7-chloro-1,3-dihydro-3-hydroxy-5-phenyl-2H-1,4-benzodiazepin-2-one, 4-methyl-1-piperazineacetate.

10. A compound as defined in claim 1 which is a methanesulfonate salt of 7-chloro-1,3-dihydro-3-hydroxy-5-phenyl-2H-1,4-benzodiazepin-2-one, 4-methyl-1-piperazineacetate.

11. A compound as defined in claim 1 which is a hydrochloride salt of 7-chloro-1,3-dihydro-3-hydroxy-1-methyl-5-phenyl-2H-1,4-benzodiazepin-2-one, 4-methyl-1-piperazineacetate.

12. A compound as defined in claim 1 which is a methanesulfonate salt of 7-chloro-1,3-dihydro-3-hydroxy-1-methyl-5-phenyl-2H-1,4-benzodiazepin-2-one, 4-methyl-1-piperazineacetate.

* * * * *